Figure 1:
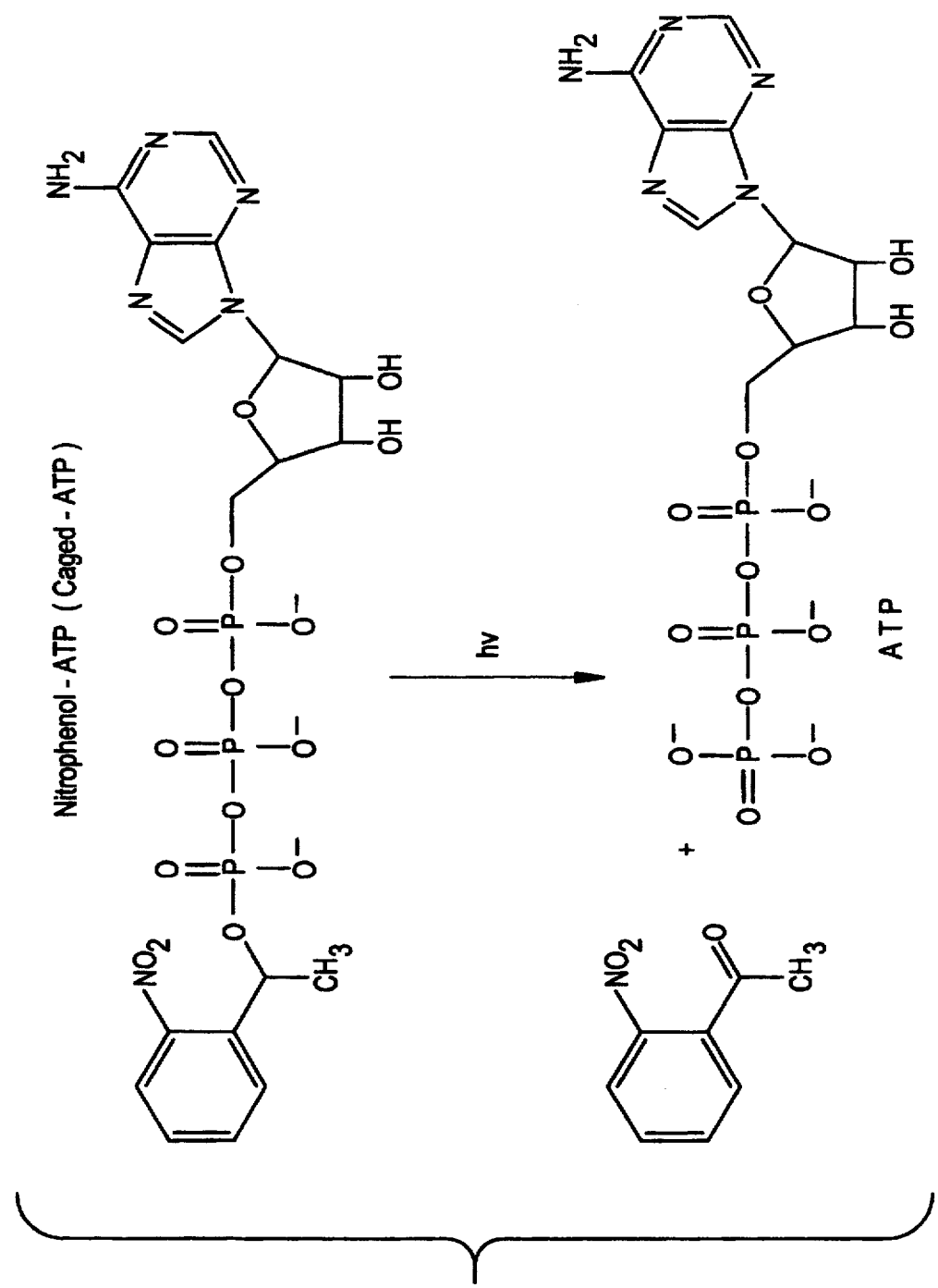

United States Patent [19]

Simpson et al.

[11] Patent Number: 5,801,007

[45] Date of Patent: Sep. 1, 1998

[54] METHODS FOR CALIBRATING CHEMICAL ASSAYS

[75] Inventors: Willaim John Simpson, Surrey; Julian Mark Pye, Ayr, both of Great Britain

[73] Assignee: BRF International, United Kingdom

[21] Appl. No.: 721,984

[22] PCT Filed: Apr. 6, 1995

[86] PCT No.: PCT/GB95/00794

§ 371 Date: Apr. 7, 1997

§ 102(e) Date: Apr. 7, 1997

[87] PCT Pub. No.: WO95/27797

PCT Pub. Date: Oct. 19, 1995

[30] Foreign Application Priority Data

Apr. 6, 1994 [GB] United Kingdom ............... 9406737.8

[51] Int. Cl.$^6$ ............... C12Q 1/66; C12Q 1/00; C12Q 1/34; C12Q 1/42

[52] U.S. Cl. ............... 435/8; 435/4; 435/968; 435/975; 435/21; 435/18; 536/26.26

[58] Field of Search ............... 435/8, 4, 968, 435/975, 21, 18; 536/26.26

[56] References Cited

U.S. PATENT DOCUMENTS

| | | | |
|---|---|---|---|
| 3,616,253 | 10/1971 | Eustachio | 435/8 |
| 4,303,752 | 12/1981 | Kolehmainen et al. | 435/18 |
| 5,366,867 | 11/1994 | Kawakami et al. | 435/8 |
| 5,366,873 | 11/1994 | Eden et al. | 435/34 |

FOREIGN PATENT DOCUMENTS

| | | |
|---|---|---|
| 0233403 | 8/1987 | European Pat. Off. . |
| 0309429 | 3/1989 | European Pat. Off. . |

OTHER PUBLICATIONS

Little et al. (1985) J. Food Protection 48:1022–4.
Denburg et al. (1970) Arch. Biochem. Biophys. 141:668–75.
Jago et al. (1989) In "ATP luminescence: Rapid Methods in Microbiology", Soc. Appl. Bacteriol. Tech. Series, vol. 26, Stanley P.E. et al. (eds), pp. 53–61.
Simpson et al. (1991) J. Chemilumin. Biolumin. 6:97–106.

*Primary Examiner*—Louise N. Leary
*Attorney, Agent, or Firm*—Klauber & Jackson

[57] ABSTRACT

Methods for internally and externally photostandardizing chemical assays, e.g. an ATP-bioluminescence assay. A pre-determined amount of a photosensitive derivative of the analyte of interest is used in the assay protocol which releases a known amount of the free analyte when it is exposed to a flash of visible light of pre-determined duration and intensity. By monitoring the response of a test property of the assay to the release of a known quantity of analyte, a standard value can be calculated which allows either direct determination of the amount of analyte originally present in the assayed sample or production of a photocalibration series against which results of an assayed sample can be compared.

19 Claims, 4 Drawing Sheets

METHODS FOR CALIBRATING CHEMICAL ASSAYS

The present invention relates to method for calibrating chemical assays and more particularly but not exclusively to a method for calibrating assays for analytes of importance in analytical microbiology such as an assay for adenosine 5'-triphosphate (ATP).

Accurate detection and quantification of particular substances or microorganisms for analytical purposes are essential laboratory tools. Detection and quantification of contaminant substances or contaminant microorganisms for the purposes of product or process control, or for food safety reasons, are of paramount importance to the food and beverage industries. Microbial biomass estimation is also important in a number of other applications, including control of waste processing, monitoring or sterilization processes and monitoring of air quality. In many cases, it is advantageous to be able to estimate the degree of microbial or chemical contamination within the shortest possible period of time.

Numerous assay techniques are available for detection and quantification of analytes of interest, and examples include enzymic assays, enzyme linked immunosorbent assays (ELISA), spectrophotometric assays, luminescence assays, fluorescence assays, chromatographic assays, assays based on measurement of changes in optical rotation of test sample, ion selective assays (including titrimetric assays) and colorimetric assays. The particular assay method used mainly depends upon the analyte to be detected and quantified.

It is essential that the particular assay method chosen be as accurate and as reproducible as possible. In order to maximize the accuracy of such assays, standardization or calibration of the assay is important. A variety of factors can affect the assay reaction and may give rise to sources of error and thus the effects of these factors must be minimized or taken into account.

Standardization techniques are known which use radioactive isotopes for the purpose of standardizing the instrumentation rather than the assay per se. An example of such radioactive standardization is embodied in the Biolink Light Standard (Leaback, D H, Easy-to-use light standards as aids to luminometry, Szalay, A. A. et al (Eds) pp 33–37—Bioluminescence and Chemiluminescence, Status Report. Proceedings of VII International Symposium of Bioluminescence and Chemiluminescence John Wiles & Sons, Chichester 1993). Such standards are based upon gaseous-tritium-activated phosphors which emit light of a defined spectral range and exhibit predictable decay on long term storage. Such devices serve only to assist in calibration of the luminometers themselves.

It is equally important that the assay per se is also calibrated or standardized so that variations in sample and reagent compositions can be taken into account.

For example, adenosine 5'-triphosphate (ATP) is an important analyte in microbiological assays. ATP is found in live cells but not in dead cells and its presence in a sample can be indicative of microbial contamination.

One widely used technique for assaying ATP is an ATP bioluminescence technique.

In the presence of a purified enzyme (luciferase) from the American firefly, *Photinus pyralis*, a substrate, D-luciferin, and sufficient magnesium ions and dissolved oxygen, the following reaction takes place:

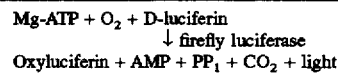

(ATP=adenosine 5'-triphosphate; Mg=magnesium ions; $O_2$=oxygen; AMP=adenosine 5'-monophosphate; $PP_i$= inorganic phosphate; $CO_2$=carbon dioxide).

Under appropriate conditions, the amount of light produced by the reaction is directly proportional to the ATP concentration and can be detected using a sensitive light detector. This is the basis of the ATP-bioluminescence assay.

Assays for ATP using the firefly luciferase reaction can be calibrated in two ways (Jago, P. H., Stanfield, G. Simpson, W. J. & Hammond, J. R. M. 1989. In ATP Luminescence: Rapid Methods in Microbiology, Society of Applied Bacteriology Technical Series, Vol. 26, Stanley P. E. et al. (eds) pp 53–61).

According to an external standardization technique, the light output from reaction of the firefly luciferase reagent with the sample can be compared to that obtained from reaction of the firefly luciferase reagent with known amount of ATP using a standard curve.

While this technique is convenient and requires a minimum of reagent manipulation, it is also subject to error. This is because the light output from firefly luciferase reactions is directly related to the rate of reaction. While the ATP concentration does indeed make a major contribution to controlling the reaction rate, it is not the sole determinant. Inhibitors present in the sample (eg. metal ions, hydrogen ions) can reduce reaction rate, and stimulators such as detergents can increase reaction rate (Simpson, W. J. and Hammond, J. R. M. 1991, *Journ. Chemilumin. & Biolumin.*, 6, 97–106). In addition, the inherent activity of the firefly luciferase reagent itself may vary due to inconsistencies in production or handling. Even though the reaction rate may be unaffected, there may be substances present in the reaction mixture which absorb the light produced to a significant extent, thus introducing error. Some substances, notably $Zn^{2+}$, in addition to reducing the catalytic activity of firefly luciferase also change the wavelength of the light produced in the reaction. This can cause a reduced amount of light to be detected from the reaction in some types of luminometers (Denburg, J. L. & McElroy, W. D. 1978. *Arch. Biochem. Biophys.* 141, 668–675).

All of these sources of error can be eliminated if the standard curve approach is abandoned in favour of the internal standardization technique, In its simplest form, this consists of adding a known amount of ATP, contained in a small volume of liquid, to an initiated firefly luciferase reaction. The light output from sample and luciferase alone, and from sample and luciferase and ATP are compared, and the ATP content of the sample then calculated. This method frees the operator of analysis errors associated with variable sample composition.

The cornerstone of this technique however, is the use of a stable ATP standard solution. A great deal of controversy exists with regard to the stability of such ATP standard solutions. Some workers claim that such dilute solutions of ATP are unstable and must be kept away from light and/or stored on ice. Also problems can be experienced due to poor handling of the solution. By far the largest threat to the stability of ATP standard solutions is the presence of contaminant microorganisms in the solution. ATP is rapidly utilized by many microorganisms (Karl, D. M. 1980. *Microbiol. Rev.* 44, 739–796), and therefore their exclusion from ATP standard solutions is essential. Aseptic technique is mandatory. Although pre-weighed vials of ATP can be purchased from some specialist luminescent reagent manufacturers, their use is not widespread on account of these perceived limitations. These problems become all the more important when ATP-bioluminescence assays are employed in safety-critical areas such as monitoring of food hygiene and air quality.

Although illustrated by the ATP-bioluminescence technique, the problems of standardizing an assay equally apply to other assay methods.

It is an object of the present invention to ameliorate the problems of standardizing chemical assays by the use of an internal photostandardization technique.

According to the present invention there is provided a method for internally standardizing a chemical assay comprising the steps:

(i) adding a pre-determined amount of photosensitive derivative of an analyte to a sample to be assayed.

(ii) measuring a test property of the assay;

(iii) exposing the sample/photosensitive derivative mix to a flash of visible light of pre-determined duration and intensity to release from the photosensitive derivative a known amount of analyte;

(iv) re-measuring the test property;

(v) repeating steps iii) and iv) inclusive from zero-n times as desired;

(vi) calculating the change in the test property measurements; and (vii) using the calculated value(s) from step (vi) as a standard to determine the amount of analyte originally present in the sample.

It is another object of the present invention to ameliorate the problems of standardizing chemical assays by production of a photocalibration series.

According to another aspect of the present invention there is provided a method for externally standardizing a chemical assay comprising the steps:

(i) exposing a pre-determined amount of photosensitive derivative of an analyte to a flash of visible light of pre-determined duration and intensity to release from the photosensitive derivative a known amount of analyte;

(ii) measuring a test property of the assay;

(iii) repeating steps (i) and (ii) inclusive from zero-n times as desired;

(iv) calculating the change in the test property measurements; and (v) using the calculated values from step (iv) as a standard against which results of an assayed sample can be compared.

Preferably the photosensitive derivative is in solution prior to the photolysis step, although in some circumstances it may be desirable to use the photosensitive derivative in a dried state.

In circumstances where a multi-point calibration procedure is desired the intensity and/or duration of the flash of visible light in step (iii) may be varied so as to compensate for a diminishing amount of photosensitive derivative available for photolysis.

It is a further object of the present invention to provide a method of standardizing an ATP-bioluminescence assay.

According to a further aspect of the present invention there is provided a method for standardizing an ATP-bioluminescence assay comprising the steps:

(i) incorporating a pre-determined amount of a photosensitive derivative of ATP into a firefly luciferase-luciferin reagent, (ii) measuring the light emitted by the reagent;

(iii) mixing a sample to be assayed with the reagent;

(iv) re-measuring the light emitted by the luminescent reaction;

(v) exposing the sample/reagent mixture to a flash of visible light of pre-determined duration and intensity to release from the photosensitive derivative a known amount of ATP;

(vi) re-measuring the light emitted by the luminescent reaction;

(vii) repeating steps v) and vi) inclusive from zero-n times as desired;

(viii) calculating the change in the light emission measurements; and (ix) using the calculated value(s) from step (viii) as a standard to determine the amount of ATP originally present in the sample.

The present method, a non-radioactive, photostandardization technique, provides advantages over previously available standardization methods in respect of (i) precision and accuracy of results; (ii) verification of results; and (iii) user friendliness.

Enhanced precision results from the elimination of pipetting errors associated with analyte standard addition, and from compensation for any changes in optical or catalytic quenching associated with assay dilution. The ability to apply a simple, valid standardization protocol is likely to give benefits in the form of facilitated result verification, a point of particular significance with respect to Food and Standards legislation and certain safety-critical applications. Improved user friendliness results from the facts that no separate analyte standard solution is necessary to perform such assays, and that the assay reagents can be factory calibrated. Furthermore, standardization of the assay may be completely independent of the method used to detect or quantify the analyte of interest.

A range of synthetic compounds of biological interest has been developed for use in physiological studies which contain a photo-sensitive chemical bond. When one of these compounds is exposed to a brief flash of intense light, a reaction product is released. The photo-sensitive compound is referred to as a 'caged' compound, from which a molecule or ion of interest can be liberated. Hence, ATP is released from caged-ATP, $Ca^{2+}$ is released from caged-$Ca^{2+}$, and so on. Such photosensitive analyte derivatives are suitable for the present invention and their use, together with a high intensity photoflash lamp or Q-switched frequency-doubled laser provides a convenient and non-invasive means for standardizing a chemical assay. The finding that commercially available photoflash lamps can effect efficient release of analyte molecules from caged precursors is hitherto unknown.

According to a first preferred method of the present invention a predetermined amount of the 'caged' compound can be added to the sample to be assayed, or to the buffer used to dilute the sample to be assayed. A particular test property of the assay is then measured. The test property measured depends upon the assay in question but it could be emitted light, heat evolution, colour changes or other properties.

A predetermined amount of the free compound is then released from the caged compound by exposing the mixture to a light flash of predetermined intensity and duration. The test property may then be re-measured and the change in test property measurements may be calculated. The calculated value may then be used as a standard to determine the amount of analyte originally present in the sample.

Alternatively, in another preferred method of the present invention, a range or standard concentrations of the compound of interest can be produced by varying the degree of photolysis in a single strength solution of a 'caged' compound. In this way, a calibration series can be prepared, for example on a microtitre plate, without the need to pipette different volumes of standard analyte solutions. In this format, for test assays, the conventional assay procedure could be followed but in selected assays, standardization could be achieved by photolysis of the 'caged' analyte prior to performing the assay step.

Accordingly, this general photostandardization system can be used with a wide variety of assay systems, including enzyme linked immunosorbent assays (ELISA), enzymic assays, spectrophotometric assays, fluorescence assays, assays based on measurement of changes in optical rotation of the test-sample, ion-sensitive assays (including titrimetric assays) and colorimetric assays.

In cases where maximum possible precision and accuracy are required of test procedures, it may be desirable to perform a multi-point calibration, rather than a single-point calibration. This can be achieved by generating a calibration series by separately photolysing different solutions of a single-strength 'caged' compound (ideally in a microtitre plate or its equivalent). By varying the degree of photolysis, for example by employing one, two, three or four flashes of pre-determined intensity and duration, a set of calibration standards is obtained.

However, this approach is not suitable where the measurement and calibration must take place in the same tube, in a non-invasive manner and where the analyte must be present at a specific step of the assay protocol such as the beginning of the protocol. It is possible, however, to perform a multi-point calibration in some single tube assays such as an ATP-bioluminescence assay. This results from the fact that such assay protocols are robust to the point at which the analyte is released into the test solution. Under some circumstances, multi-point calibration of single tube assays may be superior in terms of accuracy and precision to single point calibration of such tests.

In devising such procedures it is important to optimise the relationship between the total amount of 'caged' material available for photolysis and the intensity of the light source. In the case of assays which are standardized by means of a single-point calibration procedure, it is desirable to use as little 'caged' material as possible in the reaction and to maximise the conversion of 'caged' material to analyte by using light of sufficient intensity to release >50% of the analyte from the 'caged' material. However, in the case of assays which are to be standardized by means of a multi-point calibration procedure, it is essential to limit the conversion of 'caged' analyte to free analyte by using light of an intensity which is only capable of effecting the release of 1–2% of the analyte on exposure to the first period of photolysis. Consequently, to ensure that a sufficient amount of analyte is released, the total concentration of a 'caged' material present in the assay must be higher than is the case in reagents designed for use with single-point calibrations.

When using light flashes of fixed intensity and duration, the amount of analyte released with each sequential flash decreases. By varying the flash intensity and/or duration, it is possible to compensate for the diminishing amount of 'caged' material available for photolysis, thereby resulting in production of equal quantities of analyte at each stage and generation of linear calibration series.

In practice, the amount of analyte released under a standard set of photolysis conditions can be determined by reference to a separately-prepared standard curve prepared using a non-derivatized form of the analyte. The concentration of photosensitive analyte in the reaction can be adjusted to achieve release of a certain amount of analyte, or the intensity and/or duration of the light flash can be adjusted to achieve the same end.

Some materials phosphoresce when exposed to a high intensity flash of light, such as that produced by a flash gun. The intensity of such phosphorescence depends on the material. In tests in which estimates of analyte concentration are made by measurement of emitted light (eg. tests based on bioluminescence, chemiluminescence and fluorescence), phosphorescence is a source of interference. Ways of minimizing or correcting for such interference include the following (note that more than one strategy can be used at any one time).

A first strategy is to introduce a time delay between the period of photolysis and the period of measurement. The logarithm of the intensity of the phosphorescence decreases in proportion to the increase in the logarithm of the time elapsed. As a result, a gap of a few seconds is sufficient to reduce the measured light emission to a value which is acceptable for many types of assays.

A second strategy is to filter either the light used to irradiate the sample (or use monochromatic light such as that from a laser source) or to filter the light emitted by the cuvette material. Both strategies can be equally or differently efficacious, depending on the materials being used.

A third strategy is to select materials which have a low potential to phosphoresce when exposed to the lighting conditions specified in the photostandardization protocol.

Materials in common laboratory use differ substantially in their phosphorescence characteristics when exposed to a standard polychromatic light source in the form of a photoflash lamp.

A further strategy is to correct the result obtained after photolysis for the light emitted as a result of phosphorescence. This can be achieved using an electronic calculating device provided that (i) the inherent phosphorescence of the material is known, (ii) materials are selected to meet a standard specification and (iii) the time at which the measurements are made after exposure to light is standardized.

Most 'caged' products, whether obtained commercially, or produced in the laboratory using common-place techniques, are contaminated to a greater or lesser extent with 'uncaged' products. The presence of 'uncaged' products must be reduced to technically insignificant levels if optimal performance of the photostandardization technique is to be realized. In the case of caged-ATP, contaminant ATP molecules can be eliminated (converted to ADP and AMP which do not react with firefly luciferase) by reacting the caged-ATP with an ATP-degrading enzyme such as apyrase either in a soluble or immobilized form. Alternatively, the luciferin-luciferase reagent containing the 'caged' ATP can be incubated for 8–20 hours or more at 4° C. During this time firefly luciferase catalyses hydrolysis of ATP but does not affect the level of caged ATP. ATP can also be removed using any of the techniques currently known in preparative chemistry including chromatography, selective precipitation, or extraction. Techniques of a similar nature can be used to treat 'caged' forms of other analytes prior to use for the purposes of photostandardizing assays using, in many cases, methods that are generally known.

In some cases it may be desirable to further purify the 'caged' material. For example, in the case of a 1-(2-nitrophenyl) ethyl ester of ATP, the commercially-available material consists of a pair of diastereoisomers, since the nitrophenyl group used as the photolabile 'cage' can be added to ATP in two possible configurations. While these stereoisomers have identical photochemical properties, in some applications, advantage may be obtained by the use of only one of the stereoisomers. For example, the interaction of each stereoisomer, or more specifically its ability to form inclusion complexes, with components of the assay reagent such as α-, β-, y-cyclodextrin will differ in the case of each stereoisomer. Some commercially-available firefly luciferase reagents contain cyclodextrins (see, for example, Lundin, A, Anson, J & Kau, P ATP extractants neutralised by cyclodextrins Campbell, A K et al (Eds) pp 399–402 in Bioluminescence and Chemiluminescence, Fundamentals and Applied Aspects, Proceedings of the 8th International Symposium on Bioluminescence and Chemiluminescence, John Wiley & Sons, Chichester, 1994). Stereoisomers of caged substances can be separated from one another using well-known techniques.

It is envisaged that is some circumstances a fixed amount of the 'caged' compound can be freeze-dried onto items of equipment used to peform an assay. Examples of such items include disposable pipette tips, disposable sample cuvettes, and disposable paper discs or strips. In use, the 'caged' compound, which has been freeze-dried onto the item, dissolves when a liquid such as a test sample or analysis reagent is brought into contact with it. A pre-determined amount of the analyte can be released from the 'caged' molecule at any time by photolysis, either when the 'caged' compound is in a dried state or in solution. This type of standardization strategy is of particular value in cases where the 'caged' compound lacks adequate stability in aqueous solution. In the dried state, the stability of most 'caged' compounds to hydrolysis and oxidation is markedly increased.

In enzyme assays, such as those in which an analyte is converted to a different compound by enzymic action, conversion of the analyte may be coupled to reduction of a flavin nucleotide such as nicotinamide adenine dinucleotide, or to production of a compound such as ATP. A 'caged' form of the 'secondary' analyte (eg NADH or ATP) can be incorporated into the reaction mixture and released, when desired, by photolysis. As a result, standardization of such assays is achieved without the need to prepare separate solutions of standard material, saving both time and operator effort.

Examples of analytes which can be standardized using one or more of the aforementioned strategies include ATP, adenosine monophosphate (AMP), cyclic adenosine monophosphate (cAMP), adenosine diphosphate (ADP), guanosine triphosphate (GTP), substrates for luminogenic reactions (such as D-luciferin), inhibitors of luminogenic reactions (such as L-luciferin), organic acids (such as oxalic acid), fatty acids (such as arachadonic acid), amino acids (such as phenylalanine), sugars (such as glucose), sugar phosphates (such as glucose-6-phosphate), pesticides (such as atrazine), naturally-occurring toxicants (such as ochratoxin A), antibiotics (such as benzyl penicillin), and compounds of pharmacological interest (such as dopamine, norepinephrine, serotonin, testosterone and interferon). This list is not intended to be exhaustive, but is for the purpose of illustration.

Various photosensitive derivatives of ATP have been synthesized which release ATP. One example of these ATP derivatives is a nitrophenol ester of ATP which contains a photohydrolysable ester bond (FIG. 1). Other members of this group of compounds could be substituted for the nitrophenol. A further example of a suitable ATP derivative is 1-(4,5-dimethoxy-2-nitrophenyl) diazoethane (DMNPE).

Caged ATP has been used in a number of research applications relating to a variety of areas, including the study of muscle biochemistry. (Goldman, Y. E., Hibbard, M. G. McCray, J. A. & Trentham, D. R. 1982, Nature, 300, 701–705). It has not been previously suggested or used for the purpose of calibrating biochemical or microbiological assays.

The yield of ATP from caged-ATP has been shown to be independent of pH over the pH range 6–9; furthermore, caged-ATP has been shown to be convenient to work with in that it is soluble in water at neutral pH and is not significantly photolyzed during several minutes exposure to subdued daylight (McCray, J. A. Herbette, L. Kihara, T. & Trentham, D. R. 1980, Proc. Natl. Acad. Sci., USA, 77, 7237–7241).

In order to calibrate an ATP bioluminescence reaction in accordance with the method of the present invention a caged-ATP compound is incorporated into a firefly luciferase reagent at a pre-determined concentration. Firefly luciferase does not display any catalytic activity toward caged-ATP (see Example 1), and therefore in the absence of added ATP, no light is produced from such a luciferase preparation. The reagent may be used to perform highly sensitive assays of ATP in the following way:

A sample and the reagent are mixed in a disposable luminometer cuvette. The sample may consist of an aqueous fluid of any origin or may be a specially prepared "extract" produced as a result of treatment with any of a variety of agents designed to release ATP from living organisms. The light emitted from the luminescent reaction is measured using a luminometer. A known amount of ATP is then released into the reaction mixture by exposing the cuvette together with its contents to a flash of visible light of high intensity, delivered from e.g. a photoflash lamp. The cuvette is then placed back into the luminometer and the light emission from the luciferase reaction measured once again. Since the light flash causes the release of a known amount of ATP from the caged-ATP present, the amount of light attributable to the presence of this known amount of ATP can be calculated by difference. The amount of ATP originally present in the reaction mixture can then be calculated.

The following non-limiting Examples are intended to describe the nature of the invention more clearly:

Example 1 Use of Caged-ATP for Standardization of ATP Assays

Caged-ATP (Calbiochem, USA, prod. no. 119127, 5 mg) was dissolved in 0.5 ml sterile de-ionized water. The resulting stock solution was stored frozen at −20° C. until required. Before use, it was diluted 1 in 1000 with sterile de-ionized water. To 3 ml of a commercially-available luciferase-luciferin reagent. (Biotrace XT reagent, Biotrace Ltd., Bridgend, UK) was added 200 μl or sterile de-ionized water to form a control reagent or 200 μl of the caged-ATP stock solution to form a caged-ATP reagent. The reagents were then incubated for 1–6 hours at 20° C.

At various times, after preparation of the reagents, sterile de-ionized water (300 μl) was transferred to a clean disposable luminometer cuvette than 100 μl of control reagent of caged-ATP reagent added. The light emitted from the reaction was quantified using a Biotrace M3 Luminometer (Biotrace Ltd, Bridgend, UK), which integrated the light response for 10 seconds after a 2 second delay. A volume of ATP solution (10 μl, 0.1 μM) was then added to the reaction mixture and the light output measured for a second time. The cuvette, together with its contents, was then exposed to an intense flash of light from a Hanimex 325A2 flash gun (Hanimex, UK) and the light output from the reaction measured for a third time.

The results in Table 1 show the light output values obtained. Several points are highlighted by these results: (i) caged-ATP did not compete with ATP for the active site on firefly luciferase as indicated by the similar response observed to 1 pmol added ATP recorded for both reagents (average, n=5) of 1302 RLU from 1 pmol ATP in absence of caged-ATP and 1304 RLU from 1 pmol ATP in presence of 95.2 pmol caged-ATP); (ii) the high intensity light flash did not affect the rate of the firefly luciferase reaction as demonstrated by the fact that the response of the reagent to 1 pmol ATP was unchanged after flashing (1308 RLU before flashing, 1276 RLU after flashing: the difference can be solely attributed to the natural decay in luminescence associated with such reactions); (iii) exposure of the caged-ATP reagent to a high intensity flash of light produced an increase in ATP content in the assay, equivalent to 1.171 pmol ATP/assay. The assays could be calibrated on the basis of this response. Calibration of the assays in this way (with respect to the 1 pmol of free ATP added to the reaction) gave a value of 1.00±0.08 pmol ATP/assay (mean±S.D, n=5) with the errors randomly distributed with respect to time. In the case of the control assays, standardized by the standard curve technique (using the data at a reagent age of 1 hour), a value of 0.93±0.06 pmol ATP/assay (mean±S.D, n=5) was obtained, with the individual values showing a marked decrease with respect to time since reagent preparation (on account of a reduction in luciferase catalytic activity).

Once introduced into the luciferase reagent, caged-ATP might release ATP either by spontaneous hydrolysis, as a result of enzymic action, and/or by photolysis. The results shown in Example 1 indicate that release of ATP by the former two mechanisms is negligible and that, on exposure to a high intensity flash of light produced by a flashgun, ATP is produced rapidly from the caged-ATP present.

Notes to Table 1

1. The high intensity photoflash (provided by a Hanimex 325A2 flash gun, Hanimex, UK) did not induce luminescence from empty cuvettes, nor from cuvettes containing test solutions such as water or caged-ATP, or luciferase-luciferin reagents in the absence of caged-ATP.
2. The "ATP photostandard" (caged-ATP) produced 1.171 pmol ATP/assay on exposure to a high intensity photoflash.
   This represents a 1.23% conversion rate of the caged-ATP present in the assay.
3. Similar results were obtained when the assays were performed in the presence of a detergent-based ATP extractant (swab diluent XT, Biotrace Ltd, Bridgend, UK), instead of water, as the sample matrix indicating that the photostandardization technique is compatible with the use of such reagents.

Example 2

In a second experiment, a similar set of assays was conducted. In these experiments, the control and caged-ATP luciferin-luciferase reagents had been incubated for 6 hours prior to use. The sample mix to which the reagent was added prior to addition of ATP and/or light flashing was sterile de-ionized water, or mixtures of water and 0.1M sodium 3,3'-dimethylglutarate buffer (pM 4.00). These experimental conditions were designed to generate a range of pH values in the final assay. The results in Table 2 show that, in the presence of increasing amounts of buffer, the light output from reactions containing 1 pmol ATP was reduced. Thus, if the standard curve approach was adopted and the results referred to those obtained using water as the sample matrix, substantial errors were evident. In the extreme, a value of 0.05 pmol ATP/assay was obtained, i.e. one-twentieth of the true value. Results based on the photostandardization technique were also subject to error but of a much smaller magnitude.

The following data provide further evidence of the utility of the photostandardization technique. A luciferase/luciferin reagent which contained caged-ATP was prepared by adding caged-ATP to Biotrace MLX reagent (Biotrace, UK) to a concentration such that each 100 μl of reagent contained 43.1 pmol of caged-ATP (ie 431 nmol/l). This reagent was incubated overnight at 4° C. to reduce the background light emission. The assays were carried out as follows. ATP was added to a series of tubes (1 pmol per tube in 10 μl sterile de-ionized water) then 290 μl of trichloroacetic acid (TCA) solution in HEPES/EDTA buffer (original pH value of the buffer was 7.75) added. Final concentrations of TCA in the solution added were 2.5 g/l, 1.25 g/l and 0.25 g/l.

Luminescence was initiated in the case of each sample by adding 100 μl of the modified luciferase/luciferin reagent. The resulting light output was recorded in a Biotrace Multilite luminometer. The cuvette was then removed from the luminometer and exposed to a high intensity flash of light using a photoflash lamp which was mounted in a device of our own design (Serial number 005). The cuvette was then placed back in the luminometer and the light produced by the reaction recorded for a second time.

The ATP content of each tube was calculated on the assumption that each photolysis step resulted in formation of 1.15 pmol of ATP. All tests were carried out in duplicate. The following results were obtained.

| Concentration of TCA | RLU sample | RLU after flash | ATP in sample (pmol) |
| --- | --- | --- | --- |
| 0.25 g/l | 15339 | 33406 | 0.976 |
|  | 15172 | 32572 | 1.003 |
| 1.25 g/l | 10857 | 23117 | 1.018 |
|  | 10564 | 22990 | 0.978 |
| 2.5 g/l | 5681 | 12535 | 0.953 |
|  | 5488 | 12291 | 0.928 |

Note: results not corrected for blank reagent light output, which was insignificant.

The results shown that TCA strongly inhibited light emission when it was present at higher concentrations. Estimates of ATP content based on light emission alone would have been in serious error. However, results based on photostandardization were both reproducible and precise.

Example 3 Preparation of a Series of Standard Solutions of Known Concentration Using Caged-ATP and Varying Quanta of Light Caged-ATP (Calbiochem, USA) was dissolved in sterile de-ionized water to a final concentration of 14.4 μmol/l. Portions (300 μl) of the solution were transferred to clean disposable cuvettes then subjected to between one and 10 flashes using a Manimex flashgun. After photolysis, the solutions were analysed by adding 100 μl of luciferase/luciferin reagent (Biotrace MLX reagent, Biotrace plc, UK). The light emitted was quantified using a Biotrace Multilite luminometer which integrated the light signal for 10 seconds after a two-second delay.

Figure 2:
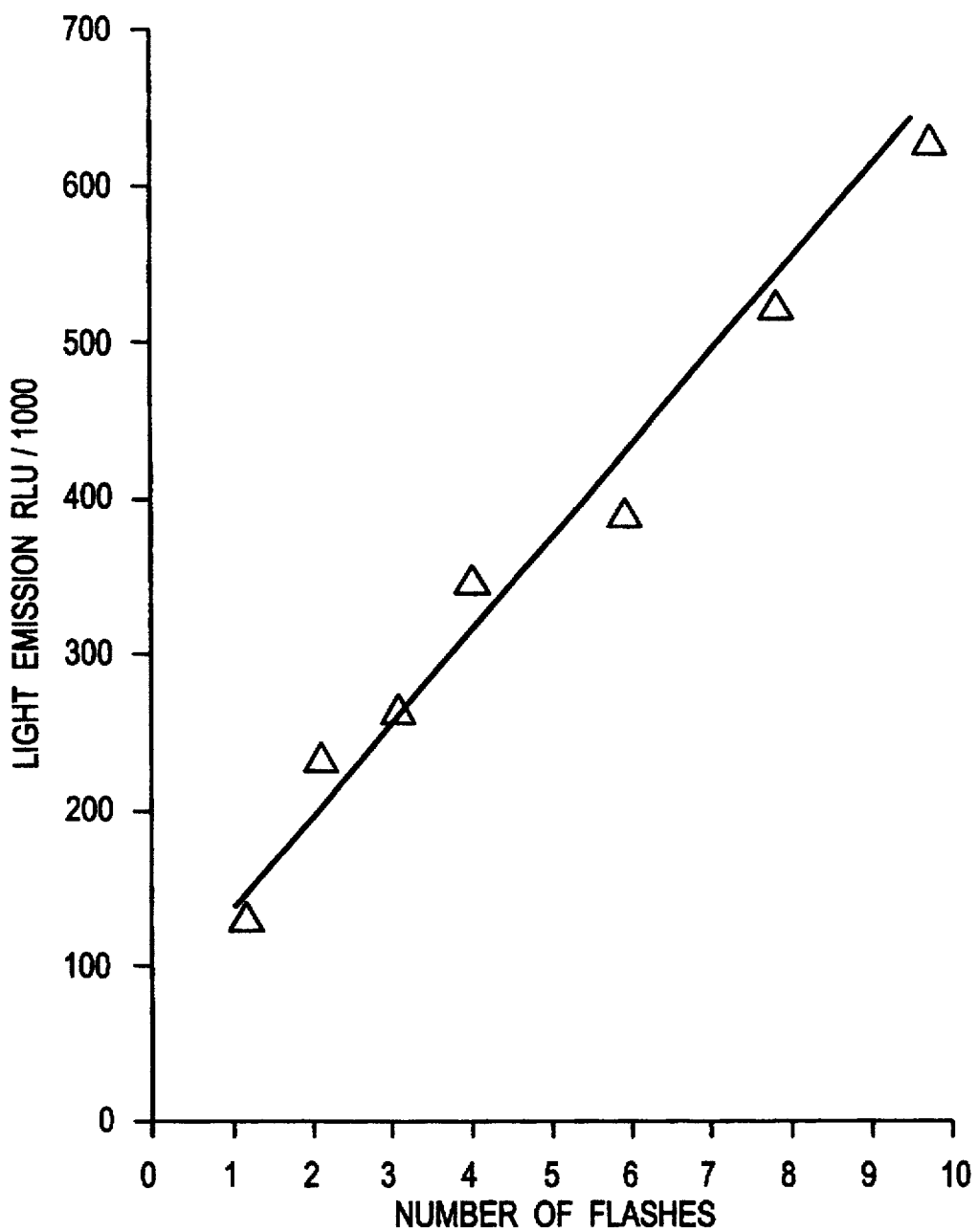

The results are shown in FIG. 2.

The results in FIG. 2 show that a 'calibration curve' could be produced in this way. This curve is analagous to that which could have been prepared by pipetting equal volumes of standard solutions of ATP, of different concentrations, into separate cuvettes. The photostandardization technique as described allowed the same result to be achieved with substantial savings in operator effort. The technique is also non-invasive in nature.

Example 4 Demonstration of Cuvette Phosphorescence

Figure 3:
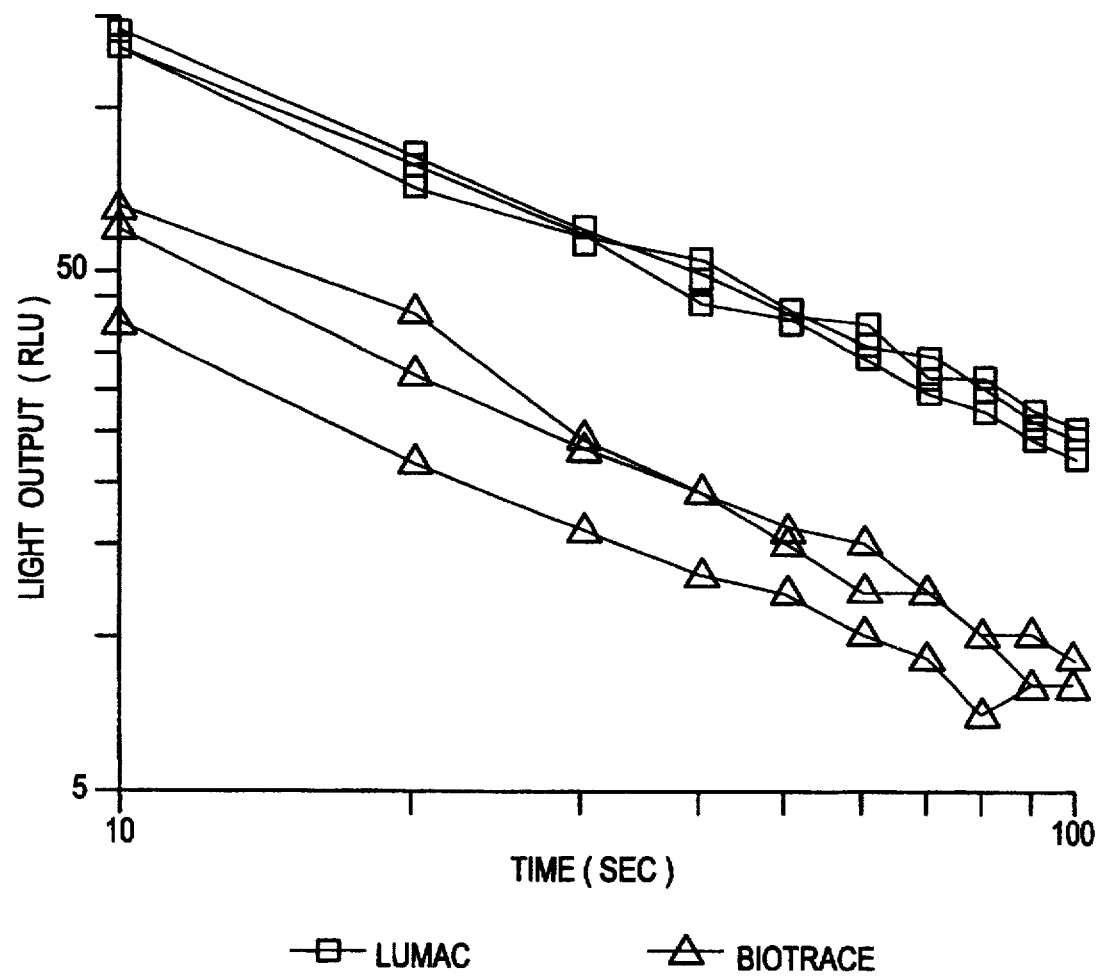

Different types of cuvettes, including those supplied by Lumac bv (Landgraaf, the Netherlands) and Biotrace plc (Bridgend, UK), were exposed to a high intensity flash of polychromatic light from a photoflash lamp mounted in a sample chamber of out own design. After exposure, each cuvette was immediately transferred to the sample chamber of a Biotrace Multilite luminometer and the resulting light emission (which was associated with phosphorescence of the cuvette material) measured over a period of 100 seconds. Each experiment was repeated three times. FIG. 3 shows decay of cuvette phosphorescence with time.

The results in FIG. 3 shows that the intensity of the phosphorescence from the Lumac cuvettes was considerably higher than that from the Biotrace cuvettes. Furthermore, the time course of the phosphorescence was consistent for cuvettes of the same type. Experiments using an anti-static mat showed that light emission from the cuvettes was not the result of a discharge of static electricity.

Figure 4:
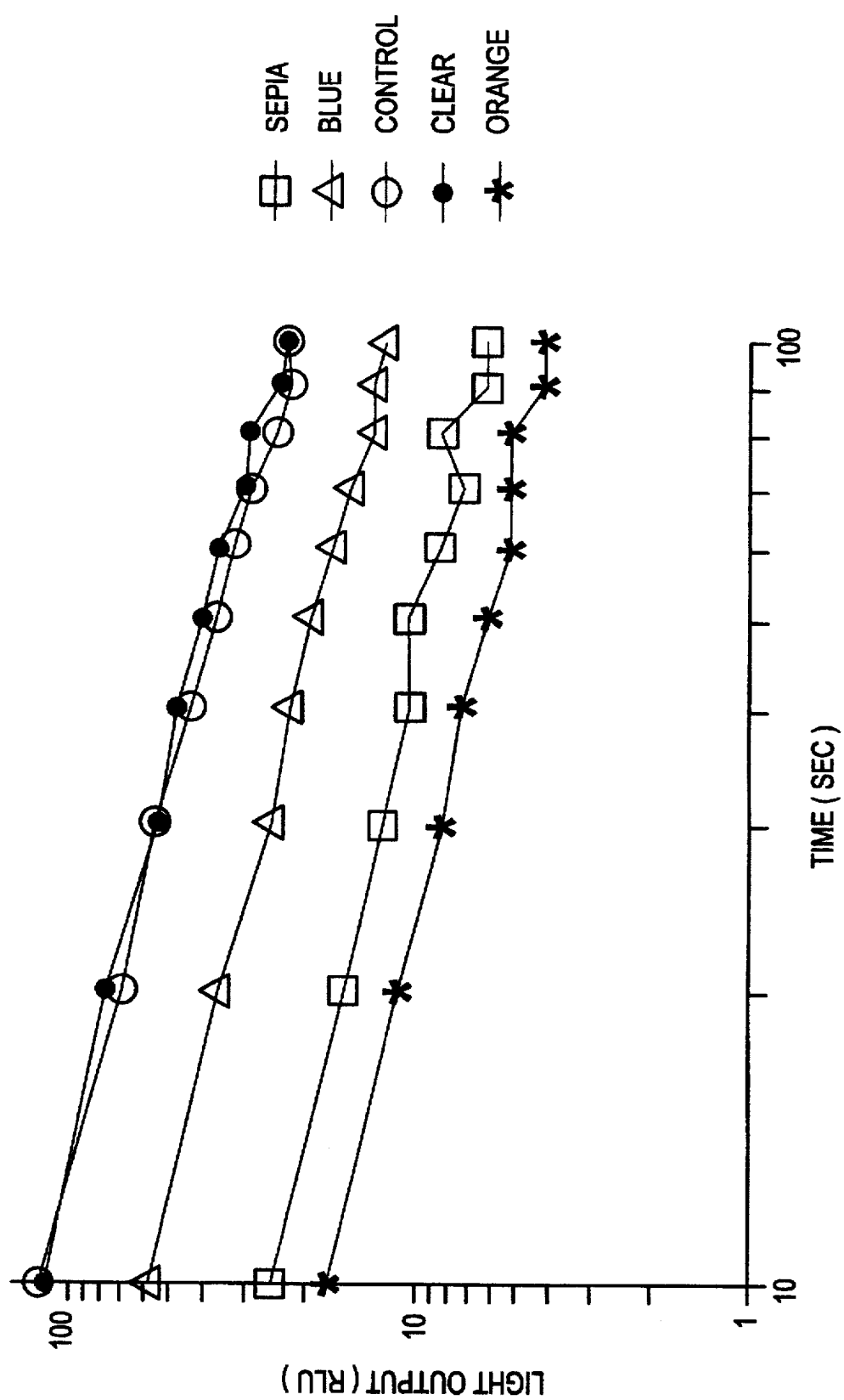

By applying various filters to the light source the degree of phosphorescence could be minimized. Cuvettes obtained from Lumac bv were exposed to a high intensity flash of light which in some cases was first of all filtered, then the cuvettes were placed in a Biotrace Multilite luminometer. The light emitted was quantified at intervals. FIG. 4 shows the decay of cuvette phosphorescence with time for cuvettes exposed to filtered light. The responses to filtered light indicated that light in the ultra-violet region of the spectrum was responsible for cuvette phosphorescence. A range of materials was examined for phosphorescence induced by unfiltered light. The initial light emission from such materials ranged from 30 RLU to 5239 RLU (measured using a 10-second integration with a Biotrace Multilite luminometer). These results demonstrate several points.

1. Phosphorescence of cuvettes can lead to significant light emission occurring from samples exposed to the lighting conditions used to photostandardize assays.
2. Different types of cuvette vary in their ability to phosphoresce after exposure to high intensity light.
3. Filtering of the light can minimize phosphorescence (though due attention must be paid to the wavelength of light required to initiate release of analyte from 'caged' material).
4. The rate of decay of phosphorescence from such cuvettes is linear when plotted as a logarithmic plot.

Example 5 Elimination of Free ATP From Caged-ATP Using an ATP-Degrading Enzyme Caged-ATP solution (14.3 mmol/l; 10 μl) was added to 1 ml Lumit buffer (HEPES/EDTA/Mg buffer, pH 7.75; Lumac bv) containing 5 μl/ml of apyrase solution. The potato apyrase was a commercial preparation (Somase) obtained from Lumac bv and was reconstituted by adding 1 ml Lumit buffer to a vial of apyrase. At various times, 20 μl of this solution was transferred to clean disposable luminometer cuvettes containing 300 μl sterile de-ionized water. The light emitted by the sample was measured using a Biotrace Multilite luminometer (Biotrace, UK). The cuvette was then removed from the luminometer and placed in a flash device of our own design. After receiving a single flash from a photoflash tube, the cuvette was returned to the luminometer and the light emission measured once again. Control experiments monitored the light output from reactions in which Lumit buffer was added to the sample of caged-ATP, rather than apyrase solution.

The following results were obtained.

|  | without apyrase | | with apyrase | |
| --- | --- | --- | --- | --- |
|  | before flash | after flash | before flash | after flash |
| 5 minutes | 389211 | >1000000 | 34844 | 837480 |
| 15 minutes | 400630 | 944471 | 1487 | 790266 |
| 30 minutes | 441410 | >1000000 | 830 | 859374 |
| 60 minutes | 413305 | 995498 | 754 | 782365 |

Note: the luminometer can not measure light outputs in excess of 1000000 RLU. Counts approaching this limit may behave in a non-linear way.

These results show that apyrase can be used to eliminate contaminant ATP from supplies of caged-ATP. Also, apyrase does not attack caged ATP. The variation in the results can be attributed to measurement errors at the high levels of ATP used.

Example 6 Standardization of Tests Using Freeze-Dried 'Caged' Material in Disposable Sample Cuvettes A solution of caged-ATP (14.3 mmol/l; 10 μl) was transferred to 1 ml HEPES/EDTA/Mg buffer, pH 7.75 (Lumit buffer, Lumac bv) and 5 μl of a solution of potato apyrase added. The potato apyrase was a commercial preparation (Somase) obtained from Lumac bv and was reconstituted by adding 1 ml Lumit buffer to a vial of apyrase. The solution of caged-ATP containing the apyrase was incubated at 20° C. for 40 min then diluted 1:1 with Lumit buffer. Portions (1 μl) of the solution were transferred to clean disposable plastic cuvettes (obtained from Biotrace plc). This procedure resulted in each cuvette containing 143 pmol of caged-ATP. The cuvettes were then placed in a vacuum desiccator and freeze-dried at −55° C. under vacuum for two hours.

After freeze-drying, the cuvettes were tested as follows. Sterile, de-ionized water (300 μl) was transferred to each cuvette than 100 μl luciferase/luciferin reagent (Biotrace MLX reagent, Biotrace plc) added. The light emitted was recorded using a Biotrace Multilite luminometer, then ATP was released from the caged-ATP present using a photoflash lamp contained in a device constructed at BRF International (Box serial number 002). The following results were obtained on replicate cuvettes,

|  | blank value (RLU) | value after flashing (RLU) |
| --- | --- | --- |
| Cuvette 1 | 2883 | 90931 |
| Cuvette 2 | 2882 | 92759 |
| Cuvette 3 | 2598 | 90078 |
| Cuvette 4 | 2944 | 84657 |

ATP could also be released from the freeze-dried material contained in the cuvettes by flashing, prior to addition of any samples or reagents to the cuvette. In performing such tests, the following results were obtained.

|  | blank value obtained after flashing dry cuvette (RLU)* | value after flashing (RLU) |
|---|---|---|
| Cuvette 1 | 49170 | 133736 |
| Cuvette 2 | 75870 | 141760 |
| Cuvette 3 | 34206 | 116517 |

*Reagents added as in previous tests.

These results show that ATP can be released from caged-ATP even in the presence of very low quantities of water. Thus, if desired, assay protocols could be devised in which ATP, or other analytes, are released from the 'caged' molecule before any liquid steps of the assay. In some cases, this may be a convenient way of standardizing certain tests.

Example 7 Preparation of a Series of Standard Solutions of Known Concentration Using Caged-Arachidonic Acid and Varying Quanta of Light Caged-arachidonic acid (Molecular Probes Inc, USA; product number A-7062) is dissolved in HEPES/EDTA buffer (pH 7.75) to a final concentration of 14.4 µmol/l. Portions (100 µl) of the solution are transferred to clean disposable tubes then subjected to between one and 10 flashes using a Hanimex flashgun. After photolysis, the solutions are analysed using any method suitable for quantification of arachidonic acid, such as HPLC, GC/MS, TLC or specific enzymic methods.

A 'calibration curve' can be produced in this way which is analogous to that which could have been prepared by pipetting equal volumes of standard solutions, of different concentrations, into separate vials. The photostandardization technique as described allowed the same result to be achieved with substantial savings in operator effort. The technique is also non-invasive in nature.

Example 8 Preparation of a Series of Standard Solutions of Known Concentration using Caged-Penicillin V and Varying Quanta of Light Caged-penicillin V (Molecular Probes Inc, USA: product number P-7061) is dissolved in HEPES/EDTA buffer (pH 7.75) to a final concentration of 14.4 µmol/l. Portions (100 µl) of the solution are transferred to clean disposable tubes then subjected to between one and 10 flashes using a Hanimex flashgun. After photolysis the solutions are analysed using any method suitable for quantification of penicillin V, for examples using an ELISA test.

A 'calibration curve' can be produced in this way which is analagous to that which could have been prepared by pipetting equal volumes of standard solutions, of different concentrations, into separate vials. The photostandardization technique as described allowed the same result to be achieved with substantial savings in operator effort. The technique is also non-invasive in nature.

Examples of other caged analytes which could be used in methods analogous to examples 7 and 8 include caged aspartic acid (Molecular Probes Inc USA: product number A-2505), caged L-lysine (Molecular Probes Inc USA: product number B-7099), caged L-epinephrine (Molecular Probes Inc USA: product number D-7057), caged L-dopamine (Molecular Probes Inc USA: product number D-7064), caged L-phenylalanine (Molecular Probes Inc USA: product number D-7093) and caged D-luciferin (Molecular Probes Inc USA: product number L-7085).

TABLE 1

Use of caged-ATP to standardize ATP assays over the course of a working day

| Time since preparation of reagent (h) | LIGHT OUTPUT (RLU*) | | | | | | CALCULATED ATP CONTENT (pmol/assay) OF STANDARD BASED ON | |
|---|---|---|---|---|---|---|---|---|
| | No added ATP | | +1 pmol ATP | | +Light Flash | | | |
| | control reagent | caged-ATP reagent | control reagent | caged-ATP reagent | control reagent | caged-ATP reagent | (i) standard arrive at T = 1 h | (ii) photo-standardization |
| 1 | 7 | 69 | 1405 | 1495 | 1419 | 3129 | 1.00 | 1.02 |
| 2 | 7 | 20 | 1372 | 1377 | 1320 | 2875 | 0.98 | 1.06 |
| 4 | 6 | 57 | 1315 | 1367 | 1308 | 3014 | 0.94 | 0.93 |
| 5 | 6 | 80 | 1262 | 1258 | 1211 | 2786 | 0.90 | 0.90 |
| 6 | 5 | 24 | 1185 | 1271 | 1121 | 2616 | 0.84 | 1.09 |
| | | | | | | $\bar{x}$ | 0.93 | 1.00 |

*RLU = relative light unit

TABLE 2

Use of caged-ATP to standardize ATP assays at different pH values

| | LIGHT OUTPUT (RLU*) | | | | | | CALCULATED ATP CONTENT (pmol/assay) OF STANDARD BASED ON | |
|---|---|---|---|---|---|---|---|---|
| | No added ATP | | +1 pmol ATP | | +Light Flash | | | |
| Test Sample Mix | control reagent | caged-ATP reagent | control reagent | caged-ATP reagent | control reagent | caged-ATP reagent | (i) standard arrive at T = 1 h | (ii) photo-standardization |
| Sterile de-ionized water | 6 | 24 | 1185 | 1271 | 1121 | 2616 | 1.00 | 1.09 |
| Water/NaDMG¹ buffer (250:50) | 9 | 21 | 949 | 871 | 912 | 2427 | 0.80 | 0.64 |
| Water/NaDMG¹ buffer (150:150) | 10 | 13 | 378 | 430 | 392 | 1058 | 0.31 | 0.78 |
| Water/NaDMG¹ buffer (0:300) | 8 | 8 | 72 | 65 | 84 | 217 | 0.05 | 0.44 |

*RLU = relative light unit
¹NaDMG = 0.1M sodium 3,3'-dimethylglutarate buffer, pH 4.00

We claim:

1. A method for internally standardizing a chemical assay comprising the steps:
   i) adding a pre-determined amount of photosensitive derivative of an analyte a sample to be assayed;
   ii) measuring a test property of the assay;
   iii) exposing the sample/photosensitive derivative mix to a flash of visible light of pre-determined duration and intensity to release from the photosensitive derivative a known amount of analyte;
   iv) re-measuring the test property;
   v) repeating steps iii) and iv) inclusive from zero-n times as desired;
   vi) calculating the change in the test property measurements; and
   vii) using the calculated value(s) from step (vi) as a standard to determine the amount of analyte originally present in the sample.

2. The method according to claim 1 wherein the photosensitive derivative of the analyte is a caged form of the analyte.

3. The method according to claim 2 wherein the derivative of the analyte is pre-treated to reduce contamination by uncaged forms of the derivative of the analyte.

4. The method according to claim 2 wherein the caged form of the analyte is freeze-dried onto a carrier.

5. The method according to claim 1 including an additional step to compensate for any inherent phosphorescence of assay materials or equipment.

6. A method of externally standardizing a chemical assay comprising the steps:
   i) exposing a pre-determined amount of photosensitive derivative of an analyte to a flash of visible light of pre-determined duration and intensity to release from the photosensitive derivative a known amount of analyte;
   ii) measuring a test property of the assay;
   iii) repeating steps i) and ii) inclusive from zero-n times as desired;
   iv) calculating the change in the test property measurements; and
   v) using the calculated values from step (iv) as a standard against which results of an assayed sample can be compared.

7. The method according to claim 6 wherein the photosensitive derivative of the analyte is a caged form of the analyte.

8. The method according to claim 7 wherein the derivative of the analyte is pre-treated to reduce contamination by uncaged forms of the derivative of the analyte.

9. The method according to claim 7 wherein the caged form of the analyte is freeze-dried onto a carrier.

10. The method according to claim 6 including an additional step to compensate for any inherent phosphorescence of assay materials or equipment.

11. A method for standardizing an ATP-bioluminescence assay comprising the steps:
    i) incorporating a pre-determined amount of a photosensitive derivative of ATP into a firefly luciferase-luciferin reagent,
    ii) measuring the light emitted by the reagent;
    iii) mixing a sample to be assayed with the reagent;
    iv) re-measuring the light emitted by the luminescent reaction;
    v) exposing the sample/reagent mixture to a flash of visible light of pre-determined duration and intensity to release from the photosensitive derivative a known amount of ATP;
    vi) re-measuring the light emitted by the luminescent reaction;
    vii) repeating steps v) and vi) inclusive from zero-n times as desired;
    viii) calculating the change in light emission measurements; and
    ix) using the calculated value(s) from step (vii) as a standard to determine the amount of ATP originally present in the sample.

12. A method according to claim 11 wherein the photosensitive derivative of ATP is a caged form of ATP.

13. A method according to claim 12 wherein the caged form of ATP is a nitrophenol ester of ATP.

14. The method according to claim 12 wherein the luciferase-luciferin reagent containing the caged form of ATP is pre-treated by incubation for 8–20 hours or more at 4° C.

15. The method according to claim 12 wherein the caged from of ATP is pre-treated with an ATP degrading enzyme.

16. The method according to claim 11 including an additional step to compensate for any inherent phosphorescence of assay materials or equipment.

17. The method according to claim 12 wherein the caged form of ATP is freeze-dried onto a carrier.

18. A kit for standardizing an ATP bioluminescence assay comprising:

1) an assay buffer;
2) a photosensitive derivative of ATP; and
3) a firefly luciferase-luciferin reagent.

19. The kit according to claim 18 further comprising:

4) a luminometer; and
5) a high intensity light source.

* * * * *